(12) United States Patent
Pavliv

(10) Patent No.: US 8,399,445 B2
(45) Date of Patent: Mar. 19, 2013

(54) ACETYLCYSTEINE COMPOSITION AND USES THEREOF

(75) Inventor: Leo Pavliv, Cary, NC (US)

(73) Assignee: Cumberland Pharmaceuticals, Inc., Nashville, TN (US)

( * ) Notice: Subject to any disclaimer, the term of this patent is extended or adjusted under 35 U.S.C. 154(b) by 0 days.

(21) Appl. No.: 13/406,175

(22) Filed: Feb. 27, 2012

(65) Prior Publication Data

US 2012/0309832 A1 Dec. 6, 2012

Related U.S. Application Data

(62) Division of application No. 11/209,804, filed on Aug. 24, 2005, now Pat. No. 8,148,356.

(51) Int. Cl.
*A61K 31/33* (2006.01)

(52) U.S. Cl. .................................................. 514/183

(58) Field of Classification Search ................... 514/183
See application file for complete search history.

(56) References Cited

U.S. PATENT DOCUMENTS

| 4,849,452 | A | 7/1989 | Dulce et al. |
|---|---|---|---|
| 5,114,974 | A | 5/1992 | Rubin |
| 5,124,351 | A | 6/1992 | Rabinovitz et al. |
| 5,206,269 | A | 4/1993 | Ludwig et al. |
| 5,272,166 | A | 12/1993 | Breslow et al. |
| 5,354,748 | A | 10/1994 | Sugita et al. |
| 5,441,748 | A | 8/1995 | Moyiyasu |
| 5,474,757 | A | 12/1995 | Yang |
| 5,691,380 | A | 11/1997 | Mason et al. |
| 5,700,653 | A | 12/1997 | Lu et al. |
| 5,807,894 | A | 9/1998 | Stroppolo et al. |
| 5,882,688 | A | 3/1999 | Alonso et al. |
| 6,103,748 | A | 8/2000 | Bryan |
| 6,114,387 | A | 9/2000 | Cutler |
| 6,149,891 | A | 11/2000 | Korenstein et al. |
| 6,281,222 | B1 | 8/2001 | Salzman et al. |
| 6,355,682 | B1 | 3/2002 | Weinberg |
| 6,468,965 | B1 | 10/2002 | Cutler |
| 6,566,401 | B2 | 5/2003 | Herzenberg et al. |
| 2001/0031737 | A1 | 10/2001 | Richardson et al. |
| 2002/0002146 | A1 | 1/2002 | Halevie-Goldman |
| 2002/0025310 | A1 | 2/2002 | Bland |
| 2002/0031513 | A1 | 3/2002 | Leibovitz |
| 2003/0176359 | A1 | 9/2003 | Neuwelt et al. |
| 2004/0022873 | A1 | 2/2004 | Guilford et al. |
| 2007/0049640 | A1 | 3/2007 | Pavliv |

FOREIGN PATENT DOCUMENTS

| AU | 2006282030 | 3/2008 |
|---|---|---|
| AU | 2011202871 | 6/2011 |
| CA | 821525 | 8/1969 |
| CA | 2526208 | 12/2004 |
| CA | 2619441 | 2/2008 |
| CN | 200680030443.9 | 2/2008 |
| CN | 201110165261.5 | 6/2011 |
| EP | 0639375 | 2/1995 |
| EP | 2006771456 | 11/2008 |
| FR | 2788436 | 7/2000 |
| GR | 1002731 | 7/1997 |
| HK | 08113428.7 | 12/2008 |
| JP | 7309746 | 11/1995 |
| JP | 2008527905 | 2/2008 |
| KR | 10-2008-7006611 | 3/2008 |
| NZ | 566100 | 2/2008 |
| NZ | 591574 | 3/2011 |
| PH | 12008500349 | 2/2008 |
| SG | 200801568-7 | 2/2008 |
| SG | 201006138-0 | 8/2010 |
| VN | 2008-00711 | 3/2008 |
| VN | 1-2011-03099 | 11/2011 |
| WO | WO0180832 | 11/2001 |
| WO | WO03011249 | 2/2003 |
| WO | WO2007024311 | 3/2007 |

OTHER PUBLICATIONS

Parry, "Effect of N-acetylcysteine on antibiotic activity and bacterial growth in vitro," Journal of Clinical Microbiology, 1977, 5(1): 58-61.
van Laar, "The role of EDTA in provoking allergic reactions to subcutaneous infusion of apomorphine in patients with Parkinson's disease: a histologic study," Movement Disorders, 1998, 13(1):52-55.
Acetadote® (Acetylcysteine) Injection Package Insert (NDA 21-539/S-004).
March, Advanced Organic Chemistry; Reactions, Mechanisms, and Structure, Wiley Interscience, 3rd Ed., 1985, p. 1092.
Dribben, W.H., et al., "Stability and Microbiology of Inhalant NAcetylcysteine Used as an Intravenous Solution for the Treatment of Acetaminophen Poisoning," Ann Emerg. Med., 2003, 42:9-13.
FDA, "Guidance for Industry Q1A(R2) Stability Testing of New Drug Substances and Products" (2003).
"Airbron," DTB 1966 4: 4.
Rock, "Citizen Petition" (May 18, 2012).
Center for Drug Evaluation and Research, "Chemistry Review NDA 21-539 Acetadote (Acetylcysteine) Injection," Jan. 9, 2003.
Ahola T, Fellman V, Laaksonen R, et al. Pharmacokinetics of intravenous Nacetylcysteine in pre-term new-born infants. Eur J Clin Pham 1999;55:645-50.
Beckett GJ, Donovan JW, Hussey AJ, Proudfoot AT, Prescott LF. Intravenous Nacetylcysteine, hepatotoxicity and plasma glutathione S-transferase in patients with paracetamol overdosage. Hum Exp Toxicol 1990;9(.3): 183-6.
Boesgaard S, Iverson HK, Wroblewski H, et al. Altered peripheral vasodilator profile of nitroglycerin during long-term infusion of N-acetylcysteine. J Amer College Cardio 1994;23:163-9.
Bergstrom L, Kagedal B, Paulsen O. Pharmacokinetics of N-acetylcysteine in man. Eur J Clin Pharmacol 1986:31 (2):217-22.
Bergstrom L, Kagedal B. Dose dependent pharmacokinetics of N-acetylcysteine after oral dosing to man. Biopharm Drug Dispos 1990;11:131-36.
DeCaro L, Ghizzi A, Costa R, et al. Pharmacokinetics and Bioavailability of oral acetylcysteine in healthy volunteers. Arzneimittel forsching 1989;39:382-6.

(Continued)

*Primary Examiner* — Brandon Fetterolf
*Assistant Examiner* — Christopher R Stone
(74) *Attorney, Agent, or Firm* — Stites & Harbison PLLC; Richard S. Myers, Jr.

(57) ABSTRACT

This invention relates to novel acetylcysteine compositions in solution, comprising acetylcysteine and which are substantially free of metal chelating agents, such as EDTA. Further, this invention relates to methods of making and using the acetylcysteine compositions. The present compositions and methods are designed to improve patient tolerance and compliance, while at the same time maintaining the stability of the pharmaceutical formulation. The compositions and methods of this invention are useful in the treatment of acetaminophen overdose, acute liver failure, various cancers, methacrylonitrile poisoning, reperfusion injury during cardio bypass surgery, and radiocontrast-induced nephropathy, and can also be used as a mucolytic agent.

16 Claims, No Drawings

OTHER PUBLICATIONS

Holdiness MR. Clinical pharmacokinetics of N-acetylcysteine. Clin Pharmacokinet 1991:20(2):123-34.

Horowitz JD, Henry CA, Syrjanen ML, et al. Combined use of nitroglycerin and Nacetylcysteine in the. management of unstable angina pectoris. Circulation 1988;77:787-94.

Horowitz RS, Dart RC, Jarvie DR, Bearer CF, Gupta U. Placental transfer of Nacetylcysteine following human maternal acetaminophen toxicity. J. Toxicol Clin Toxicol 1997;35(5):447-51.

Jones AL, Jarvie DR, Simpson D, Hayes PC, Prescott L.F. Pharmacokinetics of Nacetylcysteine are altered in patients with chronic liver disease. Aliment Pharmacol Ther 1997;11:787-91.

Lewis. PA, Woodward AJ, Maddock J, High performance liquid chromatographic assay for N-acetylcysteine in plasma and urine. J Pharm Sci 1984:73:996-8.

Olsson B, Johansson M, Gabrielsson 3, Bolme P. Pharmacokinetics and bioavailability of reduced and oxidized N-acetylcysteine. Eur J Clin Pharmacol 1988;34(1):77-82.

Prescott LF, Donovan JW, Jarvie DR, Proudfoot AT. The disposition and kinetics of intravenous N-acetylcysteine in patients with paracetamol overdosage. Eur J Clin Pharmacol 1989;37:501-06.

Rodenstein D, De Coster A, Gazzantga A. Pharmacokinetics of oral acetylcysteine: absorption, binding and metabolism in patients with respiratory disorders. Clinical Pharmacokinetics 1978;3:247-54.

Keays R et al. Intravenous acetylcysteine in paracetamol induced fulminant hepatic failure: a prospective controlled trial. BMJ 303:1926-1929, 1991.

Perry HE et al. Efficacy of oral versus intravenous N-acetylcysteine in acetaminophen overdose: results of an open-label clinical trial, J Pediatr 132:149-152, 1998.

Smilkstein MJ et al. Acetaminophen overdose: a 48 h intravenous N-acetylcysteine treatment protocol. Ann Emerg Med 20:1058-1063, 1991.

Oh TE and GM Shenfield. Intravenous N-acetylcysteine for paracetamol poisoning. Med J Aust 1:664-665, 1980.

Prescott L&F. Treatment of severe acetaminophen poisoning with intravenous acetylcysteine. Ann intern Med 141:386-389, 1981.

NDA 12-539 Approval Letter, Food and Drug Administration, 2004.

NDA 12-539 Clinical Pharmacology and Biopharmaceuitics Review.

NDA 12-539 Statistical Review.

Sagent Agila LLC's Notice of Paragraph IV Certification Regarding U.S. Patent No. 8,148,356; 2012.

NDA 12-539 Medical Review.

Mylan Institutional's Initial Non-Infringement, Invalidity, and Unenforceability Contentions, 2012.

Mylan Institutional's Notice of Paragraph IV Certification Regarding U.S. Patent No. 8,148,356; 2012.

InnoPharma, Inc.'s Notice of Paragraph IV Certification Regarding U.S. Patent No. 8,148,356; 2012.

Paddock Laboratories LLC's Notice of Paragraph IV Certification Regarding U.S. Patent No. 8,148,356; 2012.

Perrigo Research and Development Co.'s Notice of Paragraph IV Certification Regarding U.S. Patent No. 8,148,356; 2012.

Van Loenen A.C. et al., Bereiding en houdbaarheid van een acetylcystein-injectie/Formulation and shelf-life of acetylcysteine injections,: Pharm Weekbl 120:313-317 (1985).

Package insert of Fliumucil Injection. Acetylcysteine, Zambon GmbH (2000).

Merck Index 13th ed., n. 3546, pp. 620-621 (2001).

Merck Index 13th ed., n. 90, p. 17 (2001).

Handbook of Pharmaceutical Excipients, 225-228. (R. Rowe et al. eds), 4th ed. (2003).

Tepel, et al., )Prevention of Radiographic-Contrast-Agent-Induced Reductions in Renal Function by Acetylcysteine, The New England Journal of Medicine 343(3):180-184 (2000).

Package Insert of Acetadote. intravenous N-Acetylcysteine, Cumberland Pharmaceuticals, Inc. (2004).

Package insert of Parvolex Injection, Acetylcysteine, David Bull Laboratories (2001).

Package insert of Acetylcysteine Solution, USP, American Regent Laboratories, Inc. (1998).

ACETYLCYSTEINE COMPOSITION AND USES THEREOF

RELATED APPLICATIONS

This is a divisional patent application claiming priority to U.S. application Ser. No. 11/209,804 filed on Aug. 24, 2005, now allowed. The contents of 11/209,804 are incorporated herein by reference.

FIELD OF THE INVENTION

The present invention relates to acetylcysteine compositions in solution and their use. In certain embodiments of this invention, the acetylcysteine composition is substantially free of chelating agents, which does not significantly impact the stability of the formulation. In other embodiments of the invention, the acetylcysteine composition is substantially free of EDTA.

BACKGROUND OF THE INVENTION

Acetylcysteine is an antioxidant having a molecular weight of 163.2 and the following chemical structure:

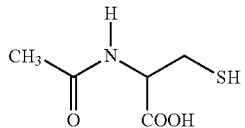

(Merck Index 13th ed., n90, page 17). Acetylcysteine is marketed generically in the United States and worldwide, as well as under the trade names of Acetadote®, Mucomyst®, Parvolex®, Fluimucil®, and others. It is approved for several indications including treatment of acetaminophen overdose, as an injectable and an oral agent, and as a mucolytic, as an inhalation product. Acetylcysteine is also being used or investigated to treat other indications including liver failure, various cancers, methacrylonitrile poisoning, reduction of radiocontrast-induced nephropathy, and reduction of reperfusion injury during cardio bypass surgery.

Acetylcysteine is not a stable molecule and is oxidized and degraded when in solution and exposed to air. Several U.S. patents have addressed this problem. For example, U.S. Pat. No. 5,691,380 appears to describe the use of a topical silicone-based emulsion system to improve the stability of acetylcysteine.

Other U.S. patents appear to address the problem by using a chelating agent to stabilize the acetylcysteine. Chelating agents, or chelators, are organic agents that bond with and thereby sequester free metal ions from solution. A widely used chelator is edetic acid or ethylenediaminetetraacetic acid, commonly referred to as EDTA, which has a molecular weight of 292.24 and the following chemical structure:

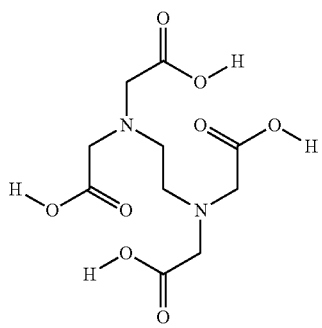 [SMILES: O=C(O)CN(CCN(CC(=O)O)CC(=O)O)CC(=O)O]

(Merck Index 13th ed., n3546, pages 620-621). EDTA is available commercially as the free acid and as various salts, for example disodium EDTA, tetrasodium EDTA, dipotassium EDTA, and calcium disodium EDTA.

U.S. Pat. No. 5,807,894, for instance, appears to describe the use of the chelating agent EDTA to improve the high reactivity of acetylcysteine in a syrup formulation. U.S. Pat. No. 6,114,387 appears to describe the use of EDTA to stabilize acetylcysteine in a solid dosage form. Aqueous solutions of acetylcysteine on the market, such as those under the trade names of Acetadote®, Mucomyst®, Parvolex®, Fluimucil®, also contain EDTA, in the form of the salt disodium edetate, which aids in stabilizing the pharmaceutical product.

While improving the stability of acetylcysteine formulations, chelating agents such as EDTA can cause undesirable effects when administered to humans or animals. Some of these undesirable effects include a significant drop in serum calcium levels (Handbook of Pharmaceutical Excipients 226 (R. Rowe et al. eds., 4th ed., 2003)), which may result in fatality, hypokalemia, hypomagnesemia, hypotension, and EDTA has also been shown to produce reproductive developmental toxicity in test animals. EDTA has also been associated with dose-related bronchoconstriction when used as a preservative in nebulizer solutions. Id. Based on the adverse effects of EDTA, particular care should be taken when administering EDTA to patients with renal impairment, liver toxicity, tuberculosis, and impaired cardiac function. Id.

Since acetylcysteine may be used to prevent or treat a variety of disorders and conditions, including liver damage, the addition of a chelating agent such as EDTA to an acetylcysteine pharmaceutical product is of concern. Chelating agents, while stabilizing the acetylcysteine composition, may also decrease the effectiveness of the composition. In addition, some individuals are allergic to chelating agents such that they cannot receive acetylcysteine compositions containing a chelating agent or may require additional care after receiving such compositions.

It would therefore be desirable to have a stable acetylcysteine solution drug product that does not produce adverse effects upon administration. In certain conditions, such as the use of acetylcysteine to lessen or prevent the liver damage caused by acetaminophen overdose, removing EDTA or other chelating agents could improve efficacy by limiting any additional liver toxicity resulting from the chelating agent.

SUMMARY OF THE INVENTION

It has been surprisingly found that an aqueous composition containing acetylcysteine, sterilized water, and a pH-adjusting agent, is stable without the addition of a chelating agent. Thus, the present invention relates to a solution containing acetylcysteine, which is substantially free of chelating agents.

The pH of the aqueous pharmaceutical composition of the invention may be from 5 to 9, from 6 to 8, from 6.5 to 7.0, or 6.8. The pH of the composition may be adjusted by the addition of a pH-adjusting agent, such as sodium hydroxide.

In one embodiment of the present invention the aqueous pharmaceutical composition is substantially free of chelating agents. In a further embodiment of the present invention, the aqueous pharmaceutical composition is substantially free of EDTA, or pharmaceutically acceptable salts thereof.

In further embodiments of the invention, the aqueous pharmaceutical composition contains less than 0.05%, less than 0.02%, or no chelating agents. In still other embodiments of the invention, the aqueous pharmaceutical composition contains less than 0.05%, less than 0.02%, or no EDTA or pharmaceutically acceptable salts thereof.

In yet another embodiment of the invention, the aqueous pharmaceutical composition consists of from 10 to 400 mg/mL acetylcysteine and an adequate amount of sodium hydroxide, dissolved in deaerated water, to achieve a final pH from 6 to 8.

Another embodiment of the present invention is a method of making an aqueous pharmaceutical composition comprising acetylcysteine, wherein the pH of the composition is from 6 to 8 and wherein the composition contains less than 0.05% chelating agents or is substantially free of chelating agents, such as EDTA.

Still other embodiments of the present invention are to methods of treating acetaminophen overdose, liver failure, various cancers, methacrylonitrile poisoning, reduction of radiocontrast-induced nephropathy, reduction of reperfusion injury during cardio bypass surgery, and diseases where a mucolytic is desired comprising administering an aqueous pharmaceutical composition comprising acetytcysteine, wherein the pH of the composition is from 6 to 8 and wherein the composition contains less than 0.05% chelating agents or is substantially free of chelating agents, such as EDTA.

Additional objects and advantages of the invention will be set forth in part in the description which follows, and in part will be obvious from the description, or may be learned by practice of the invention. The objects and advantages of the invention will be realized and attained by means of the elements and combinations particularly pointed out in the appended claims.

It is to be understood that both the foregoing general description and the following detailed description are exemplary and explanatory only and are not restrictive of the invention, as claimed.

DETAILED DESCRIPTION OF THE INVENTION

A. Definitions

In order that the present invention may be more readily understood, certain terms are first defined. Additional definitions are set forth throughout the detailed description.

The term "stable" or "stability" refers to both the physical and chemical stability of a composition in any form, such as a solution. A composition is stable if it exhibits minimal change over time relative to when it is manufactured. Stability is measured at various time points through a planned product expiration date with evaluation criteria including such items as therapeutic activity, appearance, levels of particulate matter, pH, content of active ingredient(s), and levels of degradation products, impurities, or related substances. The stability of a composition can be measured as described in Example 3.

As used herein, the term "salt" or "pharmaceutically acceptable salt" refers to acidic salts formed with inorganic and/or organic acids, as well as basic salts formed with inorganic and/or organic bases. Examples of these acids and bases are well known to those of ordinary skill in the art. Salts according to the present invention may be used in a variety of forms. In water and other aqueous solutions, salts typically dissociate into an "anion," or negatively charged subcomponent, and a "cation," or positively charged subcomponent. The salts may also be those that are physiologically tolerated by a patient, for example without undue toxicity, incompatibility, instability, and allergic response.

The term "substantially free" refers to compositions that have significantly reduced levels of chelating agents. In one embodiment, chelating agents are not added to the composition, but may be present otherwise. For instance, the chelating agent may be present as an impurity or undesired contaminant.

B. Description of the Invention

The Applicant has discovered that liquid compositions of acetylcysteine can be produced with pharmaceutically acceptable stability in solution of at least one year at ambient conditions and six months at accelerated conditions (40° C.) without the need of a chelating agent. This stability is surprising given the generally unstable nature of acetylcysteine.

Chelating agents, or chelators, are organic agents that bond with and thereby sequester free metal ions from solution. A widely used chelator is edetic acid or ethylenediaminetetraacetic acid, commonly referred to as EDTA. Additional examples of chelating agents include, but are not limited to, diethylenetriaminepentaacetic acid (DTPA), triethylenetetraaminehexaacetic acid (TTHA), trans-1,2-diaminocyclohexane-N,N,N',N'-tetraacetic acid (CDTA), ethylenediaminedisuccinic acid (EDDS), dihydroxyethyl glycine, citric acid, succinic acid, and tartaric acid A chelator may be used in its acid form, but it may also be used as one of its salts. Salts of EDTA, for example, include edetate calcium disodium, edetate disodium, edetate sodium, edetate trisodium, and edetate dipotassium.

In one embodiment, the compositions of the invention contain no chelating agents or are substantially free of chelating agents, such as EDTA. In another embodiment the compositions of the invention contain less than 0.05% of a chelating agent, such as EDTA. For example, the composition of the present invention may contain less than 0.050%, 0.045%, 0.040%, 0.035, 0.030%, 0.025%, 0.020%, 0.015%, 0.010%, 0.0050%, 0.0025%, 0.0010% of chelating agents, such as EDTA.

Acetylcysteine is the nonproprietary name for the N-acetyl derivative of the naturally occurring amino acid, L-cysteine (also known as N-acetyl-L-cysteine and NAC). In one embodiment of the invention, the aqueous compositions of the invention comprise an effective amount of acetylcysteine. Acetylcysteine includes derivatives of acetylcysteine, and pharmaceutically acceptable salts thereof. Derivatives of acetylcysteine include, but are not limited to, esters, amides, anhydrides, and thio-esters and thio-ethers of the sulfhydryl moiety. Pharmaceutically acceptable salts of acetylcysteine and acetylcysteine derivatives include, but are not limited to, sodium salts, potassium salts, magnesium salts, calcium salts, zinc salts, and ammonium salts.

The amount of acetylcysteine may vary depending on the desired characteristics of the solution and can be determined by one of ordinary skill in the art. In one embodiment of the invention, the acetylcysteine comprises 0.1-50%, in another embodiment 1.0-25%, in an additional embodiment 10%, and in yet another embodiment 20%.

The present inventor has further discovered that a liquid composition of acetylcysteine can be produced, which is substantially free of or contains less than 0.05% chelating agents, which has a pH that is suitable for injection or inhalation and can also be used orally. Thus, another embodiment of the invention is a pharmaceutical composition comprising an aqueous solution of acetylcysteine, wherein the pH of the composition is from 5 to 9. In yet another embodiment of the invention, the pharmaceutical composition comprises an aqueous solution of acetylcysteine, wherein the pH of the composition is from 6 to 8. A further embodiment of the invention is a pharmaceutical composition comprising an aqueous solution of acetylcysteine, wherein the pH is about 6.8. In still other embodiments, the pH of the composition is 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, or 9.0.

Formulations of the present invention may further comprise pH-adjusting agents, for example, basic agents. Such agents include a number of inorganic or organic bases which are pharmaceutically acceptable, in the dosage ranges used, including a monovalent metal alkali and/or a divalent metal alkali, such as, for example, sodium hydroxide solution, potassium hydroxide solution, calcium hydroxide, magnesium hydroxide, ammonia, tertiary sodium phosphate, diethanolamine, ethylenediamine, N-methylglucamine, or L-lysine and/or mixtures thereof. In one embodiment of the invention sodium hydroxide is added to the composition to adjust the pH of the composition.

The amount of pH-adjusting agent may vary depending on the desired pH of the composition and the amount of acetylcysteine in the solution and can be determined by one of ordinary skill in the art. For example, in general, the amount of a pH-adjusting agent, such as sodium hydroxide, in formulations of the present invention will directly vary depending on the desired concentration of the acetylcysteine. The exact amount of pH-adjusting agent to be employed will depend on the particular agent and upon the buffering capacity of the aqueous medium and other components of the formulation employed. Thus, the artisan will appreciate that the optimum amount of pH-adjusting agent will be readily determined, for example, by a process of titration to the desired pH.

The present invention also provides for an aqueous pharmaceutical composition consisting of from 10 to 400 mg/mL acetylcysteine and the titrated amount of sodium hydroxide or other base, dissolved in deaerated water, to achieve the desired pH of the composition, for example from 6 to 8.

In certain embodiments, the pharmaceutical composition may contain formulation materials for modifying, maintaining or preserving, for example, osmolarity, viscosity, clarity, color, isotonicity, odor, sterility, rate of dissolution or release, adsorption or penetration of the composition. In certain embodiments, suitable formulation materials include, but are not limited to, antioxidants (such as ascorbic acid or sodium metabisffuite); bulking/caking agent (such as mannitol, lactose, or trehalose); excipients and/or pharmaceutical adjuvants. (*Remington's Pharmaceutical Sciences*, 18$^{th}$ Edition, A. R. Gennaro, ed., Mack Publishing Company (1990).

The present inventor has further discovered a method of making a pharmaceutical composition comprising an aqueous solution of acetylcysteine and a pH-adjusting agent, wherein the composition is substantially free of chelating agents or contains less than 0.05% chelating agents. The method comprises the following; adding acetylcysteine to deaerated water, adding a pH-adjusting agent until a pH of approximately 6.8 is reached and the acetylcysteine is fully dissolved. Alternatively, acetylcysteine can be added to an aqueous deaerated solution containing the pH adjusting solution. The resulting product is a clear, colorless to light purple solution that can be readily passed through a sterilizing filter, such as a 0.2 micron filter. The product is then filled into vials and an inert atmosphere is placed over the solution prior to sealing. One of ordinary skill in the art will recognize methods of varying the manufacturing process to optimize the dosage form or increase the product amount for large-scale manufacturing.

Acetylcysteine administration has been shown to reduce the extent of liver injury following acetaminophen overdose. The present inventor has discovered a method of treating acetaminophen overdose comprising administering to a patient in need thereof an effective amount of a pharmaceutical composition comprising an aqueous solution of acetylcysteine, wherein the composition is substantially free of or contains less than 0.05% EDTA, or pharmaceutically acceptable salts thereof. Other conditions alleviated by the aqueous acetylcysteine compositions of the invention include, but are not limited to, liver failure, various cancers, methacrylonitrile poisoning, reduction of radio contrast induced nephropathy, reduction of reperfusion injury during cardio bypass surgery, and diseases where a mucolytic is desired.

The pharmaceutical compositions of the invention may be administered by injection (intravenous or intramuscular), by inhalation, or by the oral route. In one embodiment of the invention, the composition of the invention is dissolved in an aqueous solution containing at least one of dextrose and sodium chloride prior to administration. In another embodiment of the invention, the composition of the invention is dissolved in an aqueous solution of 0.45% or 0.90% sodium chloride (half normal and normal saline respectively). In yet another composition of the invention, it is dissolved in an aqueous solution of 5% dextrose prior to administration. The composition of the invention may also be dissolved in water for injection prior to administration. Other diluents known to those of ordinary skill in the art can also be used. Dosages of the pharmaceutical composition range from 10 mg per dose to as much as 400 mg/kg of acetylcysteine in the pharmaceutical composition and can be determined by one of ordinary skill in the art.

In one embodiment the invention, the pharmaceutical composition is administered to treat acetaminophen toxicity. The composition of the invention is mixed in 5% dextrose and 150 mg/kg of drug is given over a period of 15 minutes to 2 hours as a loading dose immediately followed by a second dose at 50 mg/kg over 4 hours and then by a third dose of 100 mg/kg over 20 hours. Additional courses can be given if required.

One of skill in the art will recognize that the appropriate dosage of the aqueous acetylcysteine compositions may vary depending on the individual being treated and the purpose. For example, the age, body weight, and medical history of the individual patient may affect the efficacy of the therapy. Further, a lower dosage of the composition may be needed to treat, for instance, lower weight patients, while heavier patients require a higher dose of acetylcysteine. A competent physician can consider these factors and adjust the dosing regimen to ensure the dose is achieving the desired therapeutic outcome without undue experimentation. It is also noted that the clinician and/or treating physician will know how and when to interrupt, adjust, and/or terminate therapy in conjunction with individual patient response.

All references cited herein are incorporated herein by reference in their entirety and for all purposes to the same extent as if each individual publication or patent or patent application was specifically and individually indicated to be incorporated by reference in its entirety for all purposes. To the extent publications and patents or patent applications incorporated by reference contradict the disclosure contained in the specification, the specification is intended to supersede and/or take precedence over any such contradictory material.

All numbers expressing quantities of ingredients, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should be construed in light of the number of significant digits and ordinary rounding approaches.

All numbers expressing percentages of ingredients, components, and so forth used in the specification and claims are to be understood as being modified in all instances by the term "w/v." Accordingly, unless indicated to the contrary, the percentages set forth in the specification and attached claims are expressed in weight per unit volume.

Many modifications and variations of this invention can be made without departing from its spirit and scope, as will be apparent to those skilled in the art. The specific embodiments described herein are offered by way of example only and are not meant to be limiting in any way. It is intended that the specification and examples be considered as exemplary only, with a true scope and spirit of the invention being indicated by the claims.

The following examples represent specific embodiments of the foregoing discovery, and they are not representative of the entire scope of the invention. The acetylcysteine, water, sodium hydroxide, and disodium edentate are Pharmacopea grade but other pharmaceutically acceptable materials can be utilized.

C. EXAMPLES

The following examples are offered for illustrative purposes only.

Example 1

Preparation of an Acetylcysteine Formulation

Twenty kilograms of acetylcysteine were added to approximately 60 liters of deaerated water for injection and the solution was mixed. A solution of sodium hydroxide was added to adjust the pH to approximately 6.5 to 7.0 and mixed until dissolved. A sufficient quantity of deaerated water for injection was added to make a 20% solution (total volume of 100 liters). Exposure to air was minimized by displacing oxygen with nitrogen. The solution was passed through a 0.2 micron sterilizing filter. The product was filled into vials or ampules and exposure to oxygen minimized by displacing the headspace with nitrogen.

Example 2

Preparation of an Acetylcysteine Formulation

Add 10 kg of acetylcysteine to approximately 60 liters of deaerated water for injection and mix. Add a solution of sodium hydroxide to adjust the pH to approximately 6.5 to 7.0 and continue mixing until dissolved. Add a sufficient quantity of deaerated water for injection to make a 10% solution (total volume of 100 liters). Minimize exposure to air by displacing oxygen with nitrogen or other pharmaceutically inert gas. Pass the solution through a 0.2 micron or other sterilizing filter. Fill the product into vials or ampules minimizing exposure to oxygen by displacing the headspace with nitrogen or other pharmaceutically inert gas.

Example 3

Stability of Acetylcysteine Compositions of the Invention

To determine whether the stability of acetylcysteine solutions required EDTA, three solutions containing different concentrations of edetate disodium were manufactured. The stability of a solution containing 0.05% edetate disodium, a solution containing 40% of that amount, 0.02% edetate disodium, and a solution containing no edetate disodium (0.00%) was examined. The three solutions were manufactured using similar processes to the process described in Example 1. Briefly, the edetate disodium, if any, was added in approximately 60% of the required deaerated water and mixed until dissolved. Acetylcysteine was then added and mixed until dissolved. The pH was adjusted to approximately 6.8 with sodium hydroxide and deaerated water was added to the target level. Nitrogen was used to purge the solutions. The product was then passed through a 0.2 micron fitter to remove potential microbial contamination and was filled into vials.

At an initial time point, high performance liquid chromatography (HPLC) was used to assess the acetylcysteine content and chromatographic purity of the three solutions. Measurements were taken of various impurities including, L-cysteine, impurity C, (disulfide), impurity D, and other impurities or degradation products. The peak areas for these HPLC measurements are presented in Table 1. An analysis of unknown peaks in the chromatograms was also undertaken. The "highest unknown" represents the area of the highest individual unidentified peak in the chromatogram, while "total unknowns" represents the total area of unidentified peaks in the chromatogram. See Table 1. In addition to HPLC, the visual appearance, pH, and levels of particulates of each of the three solutions were examined. Vials containing the three solutions were then placed at either 25° C. or 40° C. and vials were removed at 6 months, and 12 months and assayed for the parameters described above. See Table 1.

Appearance, pH, and particulate matter remained constant over time between the three formulations. As shown in Table 1, there were no significant differences between each of the three solutions in acetylcysteine content or purity. The results demonstrate that edetate is not required to produce a product with pharmaceutically acceptable stability. These results are surprising given the generally unstable nature of acetylcysteine.

TABLE 1

| Time-point | Disodium EDTA | Temp | Acetylcysteine Content | L-Cysteine | Impurity C (Disulfide) | Impurity D | Highest Unknown | Total Unknowns |
|---|---|---|---|---|---|---|---|---|
| Initial | 0.00% | N/A | 202.4 | 0.15 | 0.55 | 0.18 | 0.01 | 0.02 |
| Initial | 0.02% | N/A | 203.9 | 0.19 | 0.44 | 0.23 | 0.03 | 0.05 |
| Initial | 0.05% | N/A | 204.7 | 0.20 | 0.50 | 0.30 | 0.04 | 0.10 |
| 3 Months | 0.00% | 25° C. | 204.2 | 0.181 | 0.482 | 0.137 | 0.053 | 0.080 |
| 3 Months | 0.00% | 40° C. | 201.8 | 0.370 | 0.540 | 0.90 | 0.070 | 0.132 |
| 3 Months | 0.02% | 25° C. | 204.9 | 0.259 | 0.436 | 0.191 | 0.074 | 0.141 |
| 3 Months | 0.02% | 40° C. | 204.5 | 0.463 | 0.467 | 0.142 | 0.065 | 0.183 |
| 3 Months | 0.05% | 25° C. | 206.1 | 0.299 | 0.444 | 0.214 | 0.044 | 0.119 |
| 3 Months | 0.05% | 40° C. | 205.4 | 0.532 | 0.507 | 0.165 | 0.045 | 0.154 |

TABLE 1-continued

| Time-point | Disodium EDTA | Temp | Acetyl-cysteine Content | L-Cysteine | Impurity C (Disulfide) | Impurity D | Highest Unknown | Total Unknowns |
|---|---|---|---|---|---|---|---|---|
| 6 Months | 0.00% | 25° C. | 202.4 | 0.262 | 0.523 | 0.106 | 0.013 | 0.013 |
| 6 Months | 0.00% | 40° C. | 201.7 | 0.707 | 0.509 | 0.053 | 0.133 | 0.133 |
| 6 Months | 0.02% | 25° C. | 205.9 | 0.338 | 0.391 | 0.167 | 0.013 | 0.013 |
| 6 Months | 0.05% | 25° C. | 207.1 | 0.369 | 0.483 | 0.186 | 0.013 | 0.013 |
| 6 Months | 0.05% | 40° C. | 204.6 | 0.932 | 0.509 | 0.104 | 0.135 | 0.135 |
| 6 Months | 0.02% | 40° C. | 204.3 | 0.856 | 0.525 | 0.093 | 0.135 | 0.135 |
| 12 Months | 0.00% | 25° C. | 204.5 | 0.364 | 0.597 | 0.079 | 0.034 | 0.071 |
| 12 Months | 0.02% | 25° C. | 206.0 | 0.435 | 0.475 | 0.134 | 0.042 | 0.130 |
| 12 Months | 0.05% | 25° C. | 207.1 | 0.514 | 0.435 | 0.160 | 0.055 | 0.122 |

I claim:

1. A method of treating acetaminophen overdose, comprising:
    using a stable aqueous pharmaceutical composition comprising 200 mg/ml acetylcysteine or pharmaceutically acceptable salts thereof, wherein the composition is free of chelating agents, wherein said composition is in a suitable form for intravenous injection, wherein the pH of the composition is from 6 to 7.5, and wherein said composition is sealed in an airtight container comprising a fill volume of said composition and a headspace volume occupied by a pharmaceutically inert gas;
    diluting the composition in an aqueous solution; and
    administering the diluted composition to a patient in need thereof.

2. The method of claim 1, wherein the aqueous solution comprises at least one of 5% dextrose, 0.45% sodium chloride, and water for injection.

3. The method of claim 1, wherein the diluted composition is administered as a loading dose of 150 mg/kg, followed by a second dose of 50 mg/kg, followed by a third dose of 100 mg/kg.

4. The method of claim 1, wherein the total dose of diluted composition administered is 300 mg/kg.

5. The method of claim 1, wherein the pH of the composition is from 6.0 to less than 7.0.

6. A method of treating acetaminophen overdose, comprising:
    using a stable aqueous pharmaceutical composition comprising from 200 mg/ml to 250 mg/ml acetylcysteine or pharmaceutically acceptable salts thereof, wherein the composition is free of chelating agents, wherein said composition is in a suitable form for intravenous injection, wherein the pH of the composition is from 6 to 7.5, and wherein said composition is sealed in an airtight container comprising a fill volume of said composition and a headspace volume occupied by a pharmaceutically inert gas;
    diluting the composition in an aqueous solution; and
    administering the diluted composition to a patient in need thereof.

7. The method of claim 6, wherein the aqueous solution comprises at least one of 5% dextrose, 0.45% sodium chloride, and water for injection.

8. The method of claim 6, wherein the diluted composition is administered as a loading dose of 150 mg/kg, followed by a second dose of 50 mg/kg, followed by a third dose of 100 mg/kg.

9. The method of claim 6, wherein the total dose of diluted composition administered is 300 ma/ka.

10. A method of treating acetaminophen overdose-induced liver damage, comprising:
    using a stable aqueous pharmaceutical composition comprising 200 mg/ml acetylcysteine or pharmaceutically acceptable salts thereof, wherein the composition is free of chelating agents, wherein said composition is in a suitable form for intravenous injection, wherein the pH of the composition is from 6 to 7.5, and wherein said composition is sealed in an airtight container comprising a fill volume of said composition and a headspace volume occupied by a pharmaceutically inert gas;
    diluting the composition in an aqueous solution; and
    administering the diluted composition to a patient in need thereof.

11. The method of claim 10, wherein the pH of the composition is from 6.0 to less than 7.0.

12. The method of claim 10, wherein the aqueous solution comprises at least one of 5% dextrose, 0.45% sodium chloride, and water for injection.

13. The method of claim 10, wherein the diluted composition is administered as a loading dose of 150 mg/kg, followed by a second dose of 50 mg/kg, followed by a third dose of 100 mg/kg.

14. The method of claim 10, wherein the total dose of diluted composition administered is 300 mg/kg.

15. The method of claim 10, wherein the patient is in liver failure.

16. The method of claim 15, wherein the liver failure is acute liver failure.

* * * * *

UNITED STATES PATENT AND TRADEMARK OFFICE
CERTIFICATE OF CORRECTION

PATENT NO. : 8,399,445 B2  
APPLICATION NO. : 13/406175  
DATED : March 19, 2013  
INVENTOR(S) : Pavliv Page 1 of 1

It is certified that error appears in the above-identified patent and that said Letters Patent is hereby corrected as shown below:

In the Claims:

Column 10, line 23, cancel the text beginning with "9. The method of claim 6" to and ending with "300 ma/ka." in column 10, line 24, and insert the following claim:

--9. The method of claim 6, wherein the total dose of diluted composition administered is 300 ma/kg.--

Signed and Sealed this  
Fourth Day of June, 2013

Teresa Stanek Rea  
*Acting Director of the United States Patent and Trademark Office*

UNITED STATES PATENT AND TRADEMARK OFFICE
CERTIFICATE OF CORRECTION

PATENT NO. : 8,399,445 B2  
APPLICATION NO. : 13/406175  
DATED : March 19, 2013  
INVENTOR(S) : Pavliv It is certified that error appears in the above-identified patent and that said Letters Patent is hereby corrected as shown below:

In the Claims:

Column 10, line 23, cancel the text beginning with "9. The method of claim 6" to and ending with "300 mg/kg" in column 10, line 24, and insert the following claim:

--9. The method of claim 6, wherein the total dose of diluted composition administered is 300 mg/kg--

This certificate supersedes the Certificate of Correction issued June 4, 2013.

Signed and Sealed this  
Eighth Day of July, 2014

Michelle K. Lee  
*Deputy Director of the United States Patent and Trademark Office*